US012000696B2

(12) United States Patent
Pimentel et al.

(10) Patent No.: US 12,000,696 B2
(45) Date of Patent: Jun. 4, 2024

(54) SYSTEMS AND METHODS FOR DETECTING ANTIMICROBIAL SURFACE COATINGS

(71) Applicant: B/E AEROSPACE, INC., Winston Salem, NC (US)

(72) Inventors: Katherine Urena Pimentel, Manchester, CT (US); Steven A. Poteet, Ashland, MA (US); Thomas Martz, Winston-Salem, NC (US); David McConnell, Advance, NC (US); Vijay V. Pujar, Rancho Santa Fe, CA (US); Irene Rexwinkle, Mill Creek, WA (US)

(73) Assignee: B/E AEROSPACE, INC., Winston Salem, NC (US)

( * ) Notice: Subject to any disclaimer, the term of this patent is extended or adjusted under 35 U.S.C. 154(b) by 243 days.

(21) Appl. No.: 17/205,928

(22) Filed: Mar. 18, 2021

(65) Prior Publication Data
US 2022/0299305 A1 Sep. 22, 2022

(51) Int. Cl.
*G01B 7/06* (2006.01)
*C09D 5/14* (2006.01)
*G01N 27/04* (2006.01)

(52) U.S. Cl.
CPC ............. *G01B 7/085* (2013.01); *C09D 5/14* (2013.01); *G01N 27/041* (2013.01)

(58) Field of Classification Search
CPC ........ C09D 5/14; G01B 7/085; G01N 27/041; G01N 2033/0096; G01N 27/20; G01N 33/32; A61L 2/232; A61L 2202/25; A61L 2202/26
See application file for complete search history.

(56) References Cited

U.S. PATENT DOCUMENTS

2004/0070393 A1\* 4/2004 Sarfaty ................. G01B 7/105
324/230
2015/0361278 A1 12/2015 Call et al.
2020/0240935 A1 7/2020 Asgari et al.

FOREIGN PATENT DOCUMENTS

JP 5881236 3/2016

OTHER PUBLICATIONS

Steven A. Poteet et al., "Methods for Detecting Antimicrobial Surface Coatings Using Fluorescent Indicators," U.S. Appl. No. 17/071,781, filed Oct. 15, 2020, 20 pages.
(Continued)

*Primary Examiner* — Jay Patidar
(74) *Attorney, Agent, or Firm* — Snell & Wilmer L.L.P.

(57) ABSTRACT

A method may comprise measuring, by a conductivity or resistance measuring device, the conductivity or resistance of a surface of a substrate; comparing, by the conductivity or resistance measuring device, the measured conductivity or resistance to a reference value; and/or determining, by the conductivity or resistance measuring device, a presence or an absence of an antimicrobial system on the surface. The antimicrobial system may comprise a first coating, wherein the first coating may comprise an antimicrobial compound, wherein the antimicrobial compound may comprise a first end and a second end opposite the first end with a hydrocarbon chain therebetween, wherein the antimicrobial compound may comprise a cationic functional group on the first end and a silane group on the second end.

16 Claims, 3 Drawing Sheets

(56) References Cited

OTHER PUBLICATIONS

European Patent Office, European Search Report dated Jul. 25, 2022 in Application No. 22160340.0.
Druvari Denisa et al, "Polymeric Antimicrobial Coatings Based on Quaternary Ammonium Compounds", Coatings, DOI: 10.3390/coatings8010008, vol. 8, No. 1, Dec. 23, 2017 (Dec. 23, 2017), p. 8.

* cited by examiner

SYSTEMS AND METHODS FOR DETECTING ANTIMICROBIAL SURFACE COATINGS

FIELD

This disclosure generally relates to antimicrobial compounds on surfaces and detecting the presence or absence thereof.

BACKGROUND

Passenger compartments of vehicles (e.g., aircraft, boats, or the like) may comprise various surfaces, which are frequently touched by passengers or other people. These surfaces may be regularly cleaned or disinfected, but there is a need to mitigate or prevent the presence of microbes on these surfaces between scheduled cleanings. Therefore, being able to readily detect the presence of a previously applied antimicrobial coating or compound to the frequent touchpoint surfaces may be valuable to determine whether reapplication of such antimicrobial coating or compound is warranted.

SUMMARY

In various embodiments, a method may comprise measuring at least one of the conductivity or resistance on a surface of a substrate comprising an antimicrobial system; comparing the measured conductivity or resistance to a reference value; and/or determining a presence or an absence of the antimicrobial system on the surface. The antimicrobial system may comprise a first coating. The first coating may comprise an antimicrobial compound. The antimicrobial compound may comprise a cationic functional group on a first end of the antimicrobial compound. In various embodiments, the method may further comprise applying the antimicrobial compound to the surface to form the first coating prior to measuring at least one of the conductivity or resistance on the surface.

In various embodiments, measuring at least one of the conductivity or resistance on the surface may comprise measuring the conductivity of the first coating resulting from the cationic functional group. In various embodiments, the reference value may comprise a reference conductivity value, wherein, at least one of: in response to the measured conductivity value and the reference conductivity value differing beyond a predetermined threshold, the method may further comprise reapplying the antimicrobial compound to the surface, or in response to the measured conductivity value being less than the reference conductivity value, the method may further comprise reapplying the antimicrobial compound to the surface. In various embodiments, measuring the conductivity of the first coating may be completed via at least one of a voltmeter, a conductivity electrode, or a four-point probe.

In various embodiments, the antimicrobial system may comprise an anionic compound. In various embodiments, the anionic compound may comprise a sulfonate. In various embodiments, the anionic compound may be an anionic surfactant comprising at least one of sodium dodecyl benzene sulfonate, sodium xylene sulfonate, benzenesulfonic acid, or sodium octane-1-sulphonate monohydrate. In various embodiments, the anionic compound may be comprised in the first coating. In various embodiments, the anionic compound may be comprised in a second coating comprised in the antimicrobial system, wherein the second coating may be disposed on the first coating. In various embodiments, in response to the antimicrobial system comprising the anionic compound, the anionic compound may bind to the cationic functional group of the antimicrobial compound, deactivating a positive charge of the cationic functional group. In such embodiments, measuring at least one of the conductivity or resistance on the surface may comprise measuring the resistance of the antimicrobial system resulting from the anionic compound.

In various embodiments, the reference value may comprise a reference resistance value, wherein, at least one of: in response to the measured resistance value and the reference resistance value differing beyond a predetermined threshold, the method may further comprise reapplying the antimicrobial compound to the surface, or in response to the measured resistance value being greater than the reference resistance value, the method may further comprise reapplying the antimicrobial compound to the surface. In various embodiments, measuring the resistance of the antimicrobial system may be completed via at least one of a high resistance meter, a resistivity cell, or a four-point probe.

In various embodiments, the cationic functional group may be a quaternary ammonium group. In various embodiments, the antimicrobial compound may further comprise a second end having a silane group, which at least one of binds or couples to the surface of the substrate. In various embodiments, the second end of the antimicrobial compound is opposite the first end with a hydrocarbon chain therebetween.

In various embodiments, the surface may be comprised in an aircraft cabin, such that the surface is an aircraft cabin surface. In various embodiments, the aircraft cabin surface may be comprised in at least one of a passenger seat, a passenger suite, a passenger amenity, a control unit, a stowage/luggage compartment, a lavatory, a self-service bar or kiosk, or a galley.

In various embodiments, a system may comprise a substrate comprising a surface; an antimicrobial system disposed on the surface; and/or a device at least one of coupled to or in communication with the surface configured to measure at least one of the conductivity or resistance of the antimicrobial system. In various embodiments, the antimicrobial system may comprise a first coating comprising an antimicrobial compound. In various embodiments, the antimicrobial compound may comprise a cationic functional group on a first end of the antimicrobial compound. In various embodiments, the antimicrobial system may further comprise an anionic surfactant, and wherein the device measures the resistance of the antimicrobial system. In various embodiments, the substrate may be comprised in an aircraft and comprises at least one of a passenger seat, a passenger suite, a passenger amenity, a control unit, a stowage/luggage bin, a lavatory, a self-service bar or kiosk, or a galley.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures. Elements with the like element numbering throughout the figures are intended to be the same.

DETAILED DESCRIPTION

All ranges may include the upper and lower values, and all ranges and ratio limits disclosed herein may be combined. It is to be understood that unless specifically stated otherwise, references to "a," "an," and/or "the" may include one or more than one and that reference to an item in the singular may also include the item in the plural.

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, and mechanical changes may be made without departing from the scope of the disclosure. Thus, the detailed description herein is presented for purposes of illustration only and not of limitation. For example, the steps recited in any of the method or process descriptions may be executed in any order or combination and are not necessarily limited to the order or combination presented. Furthermore, any reference to singular includes plural embodiments, and any reference to more than one component or step may include a singular embodiment or step. Also, any reference to attached, fixed, connected, or the like may include permanent, removable, temporary, partial, full, and/or any other possible attachment option. Additionally, any reference to without contact (or similar phrases) may also include reduced contact or minimal contact.

Figure 1A:
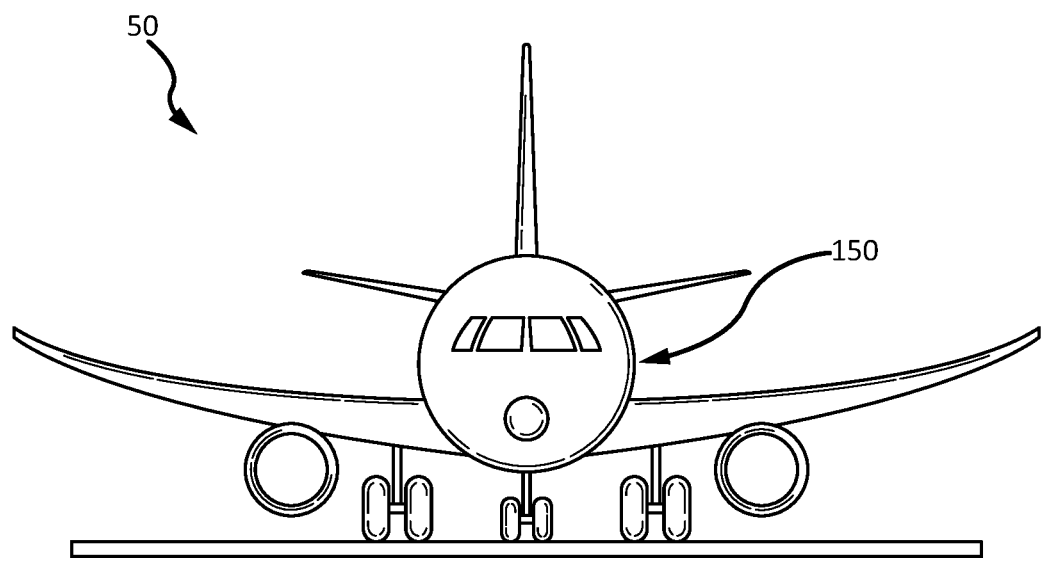
FIG. 1A illustrates a perspective view of an aircraft, in accordance with various embodiments.
Figure 1B:
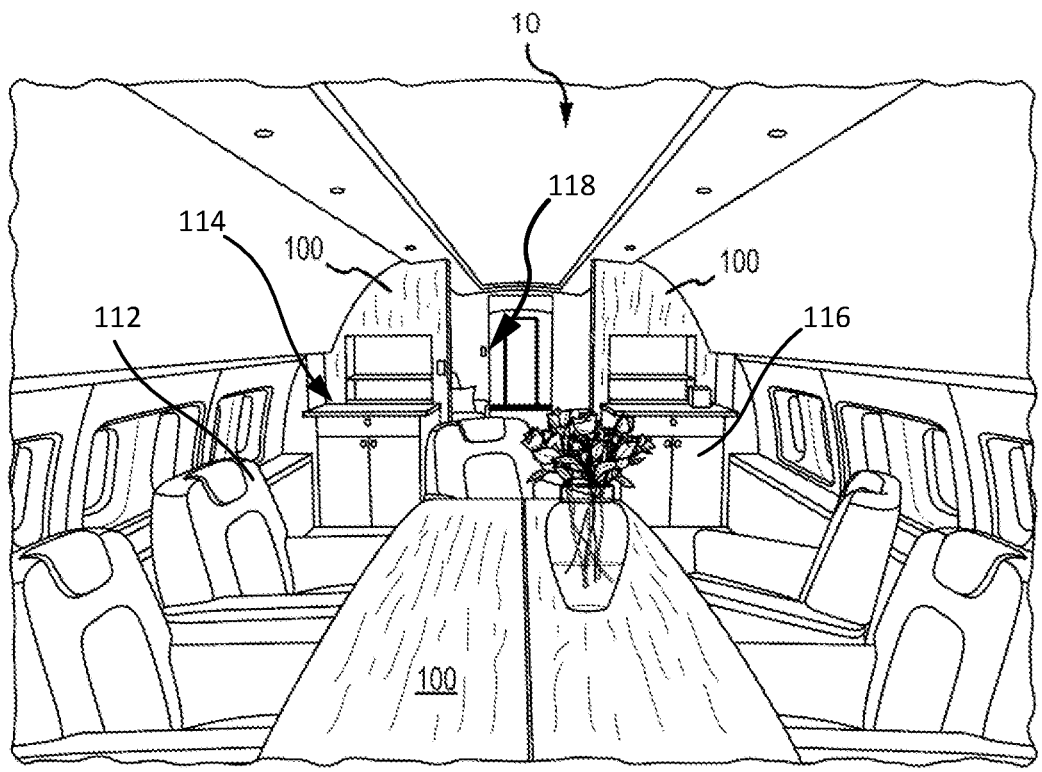
FIG. 1B illustrates a perspective view of an aircraft interior, in accordance with various embodiments.

Aircraft, such as aircraft 50 depicted in FIG. 1A, may comprise an interior cabin inside aircraft body 150. FIG. 1B depicts an interior cabin 10 inside an aircraft (e.g., aircraft 50) including various substrates having surfaces which may be frequent touchpoints by passengers or other people present in interior cabin 10. For example, the substrates having frequent touchpoint surfaces may be comprised in or on veneer panels 100 (e.g., wall or table surfaces), a passenger seat 112, a passenger amenity (e.g., a self-service bar or kiosk 114), a control unit, a stowage/luggage compartment 116, a lavatory 118, a galley, and/or the like. Other vehicles, such as automobiles and boats, may comprise the same or similar surfaces in an interior compartment.

In various embodiments, an antimicrobial compound may be applied to such frequent touchpoint surfaces. The antimicrobial compound may be configured to attract and neutralize, kill, and/or inactivate microbes (e.g., bacteria, viruses, and/or the like) that come in contact with the antimicrobial compound.

Figure 2A:
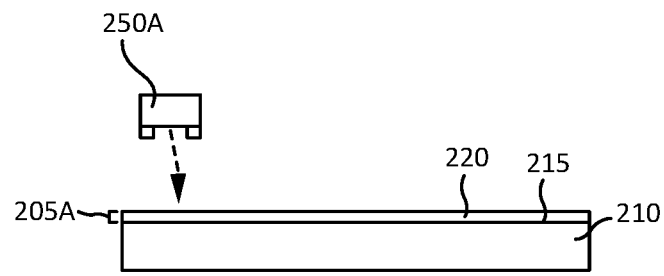
FIGS. 2A and 2B illustrate cross sectional views of substrates having antimicrobial system(s) disposed thereon, in accordance with various embodiments.
Figure 2B:
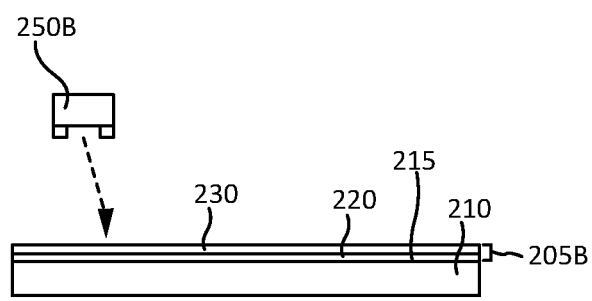

With reference to FIGS. 2A and 2B, the antimicrobial compound may be comprised in an antimicrobial system. The antimicrobial system may comprise a coating or layer disposed on a frequent touchpoint surface of a substrate. With reference to FIG. 2A, a cross section of a substrate 210 having an outer surface 215 (e.g., a frequent touchpoint surface) is depicted, in accordance with various embodiments. Substrate 210 may comprise any suitable material, such as synthetic or natural fabric surfaces, plastics, metals, composites and composite finishes, wood, glass, leather, and/or the like. In various embodiments, outer surface 215 may be the surface presented to or exposed to passengers or other people. Therefore, outer surface 215 may frequently be exposed to or receive microbes from the people coming in contact with outer surface 215, directly or indirectly.

Substrate 210 and its outer surface 215 may comprise an antimicrobial system 205A disposed thereon and/or coupled thereto. In various embodiments, the antimicrobial system 205A may comprise a first coating 220 disposed on outer surface 215. First coating 220 may be an antimicrobial coating and/or comprise an antimicrobial compound. First coating 220 and/or the antimicrobial compound may be coupled (e.g., grafted) and/or bound (e.g. via chemical, electrostatic, and/or electrochemical bonds) to outer surface 215. The antimicrobial compound may comprise any suitable compound for attracting, neutralizing, killing, and/or deactivating microbes. In various embodiments, the antimicrobial compound may comprise a cationic functional group. The cationic functional group may be comprised on a first end of the antimicrobial compound. In various embodiments, the cationic functional group may comprise a quaternary ammonium group ("QUAT"). In various embodiments, the antimicrobial compound may comprise a second end comprising a group configured to bind or couple to the substrate (e.g., a silane group). In various embodiments, the antimicrobial compound may comprise a hydrocarbon chain between the first end and the second end of the antimicrobial compound. For example, the antimicrobial compound may comprise a silane-functionalized QUAT. In various embodiments, the cationic functional group may extend outwardly from outer surface 215, such that the cationic functional group is further from outer surface 215 than the second end of the antimicrobial compound. The cationic functional group may be the portion of the antimicrobial compound extending outwardly furthest from outer surface 215. The cationic functional group may attract microorganisms (e.g., bacteria or viruses), which may be negatively charged, and then the antimicrobial compound may neutralize, kill, or deactivate such microorganism. The antimicrobial compound may couple or bind (e.g., covalently) to substrate 210, resulting in layers or coatings (e.g., first coating 220) persisting for extended periods of time (e.g., multiple months).

In various embodiments, the antimicrobial coating (e.g., first coating 220) may be a monolayer. In various embodiments, the antimicrobial coating may comprise a thickness between a single molecular layer and 0.5 micrometers (μm), or between 15 and 200 nanometers (nm). Such thicknesses of first coating 220 may cause first coating 220 to be invisible to the naked human eye, and susceptible to wear and erosion from physical contact (especially on frequent touchpoint surfaces).

Figure 3:
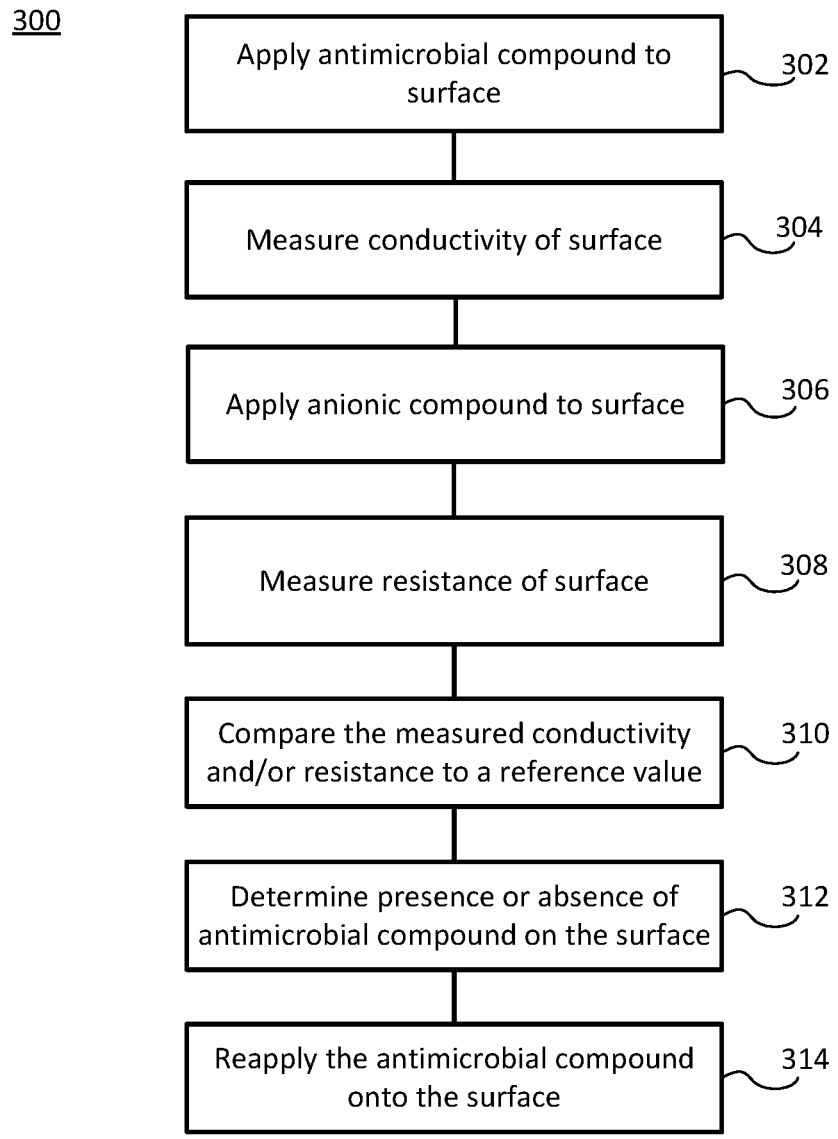
FIG. 3 illustrates a method for detecting the presence of an antimicrobial compound on a surface, in accordance with various embodiments.

With additional reference to FIG. 3, a method 300 for detecting the presence (or absence) of an antimicrobial coating (e.g., first coating 220) is valuable to indicate when reapplication of the antimicrobial compound or coating may be warranted or necessary. For example, an antimicrobial compound may be applied to outer surface 215 (step 302) of substrate 210. The antimicrobial compound may be any of those discussed herein. The antimicrobial compound may be comprised in a solution that is applied to the surface in any suitable manner, for example by spraying (e.g., electrostatic spray application), dipping, wiping, and/or the like. The antimicrobial compound or solution may be dried to form the antimicrobial coating (e.g., first coating 220) on the surface. Because first coating 220 comprises an antimicrobial compound having a cationic functional group, which may be at or proximate an outer surface of first coating 220

(opposite the inner surfaces of first coating 220 coupled to the substrate), first coating 220 and the antimicrobial compound comprised therein may conduct electricity. Therefore, by measuring the conductivity of outer surface 215 (step 304), one may be able to determine the presence (or absence) of first coating 220 and/or the antimicrobial compound on outer surface 215 (step 312).

The conductivity of surface 215 (and first coating 220 comprising the antimicrobial compound) may be measured in any suitable manner or by any suitable device (e.g., conductivity measuring device 250A). For example, the conductivity may be measured using a voltmeter, a conductivity electrode, a four-point probe, and/or the like, being applied to (e.g., coupled to and/or in communication with (e.g., electronic communication)) the surface.

In response to receiving a measured conductivity value, to determine the presence (or absence) of first coating 220 and the antimicrobial compound on outer surface 215 (step 312), in various embodiments, the measured conductivity value may be compared to a reference conductivity value (step 310). The reference conductivity value may be a value to which a measured conductivity value may be compared to aid in determining the presence (or absence) of the first coating and the antimicrobial compound on the surface. For example, the reference conductivity value of the surface may be the conductivity value that results from a freshly applied first coating comprising an antimicrobial compound (or a first coating having little or no wear or erosion), referred to herein as a baseline conductivity value. Therefore, if the measured conductivity value is less than the baseline conductivity value, it may be concluded that at least a portion of the first coating comprising the antimicrobial compound may have been removed. As another example, the reference conductivity value may be a threshold conductivity value, and in response to the measured conductivity value being less than the threshold conductivity value (or differing therefrom beyond a predetermined threshold), reapplication of the antimicrobial coating to the surface may be warranted to replenish the antimicrobial compound thereon to a desired level (e.g., such that the conductivity of the surface and the antimicrobial compound thereon is above the threshold conductivity value). As yet another example, the reference conductivity value may be a threshold conductivity differential value, which may be predetermined and/or indicate the maximum difference between the measured conductivity value and the baseline conductivity value before indicating that reapplication of the antimicrobial compound may be appropriate. That is, if the difference between the measured conductivity value and the baseline conductivity value is beyond the threshold conductivity differential value, reapplication of the antimicrobial coating may be warranted.

In response to the measured conductivity value indicating that reapplication of the antimicrobial compound may be appropriate (e.g., if there is no conductivity, or conductivity that is lower than a desired level, for example, based on comparing the measured conductivity value to the reference conductivity value), the antimicrobial compound (or a solution comprising the same) may be reapplied onto the surface (step 314).

In various embodiments, an antimicrobial system on a substrate surface may further comprise an anionic compound. Accordingly, with additional reference back to FIG. 3, detecting the presence (or absence) of the antimicrobial compound or coating on a surface (method 300) may further comprise applying an anionic compound to the surface (step 306). In various embodiments, the anionic compound may be comprised in the antimicrobial solution or coating (e.g., comprised in first coating 220). Therefore, to dispose first coating 220 onto the substrate surface, an antimicrobial compound may be combined with an anionic compound, and then such a composition may be applied to the substrate surface. In various embodiments, the anionic compound may be comprised in a coating separate from the antimicrobial coating, as depicted in FIG. 2B showing antimicrobial system 205B comprising first coating 220 having an antimicrobial compound and second coating 230 having an anionic compound disposed on first coating 220, such that first coating 220 is disposed between second coating 230 and the outer surface 215. The anionic compound may be comprised in a solution that is applied to the surface in any suitable manner, for example by spraying (e.g., electrostatic spray application), dipping, wiping, and/or the like. The anionic compound or solution may be dried to form second coating 230 on the surface.

The anionic compound may be any suitable compound. In various embodiments, the anionic compound may comprise a sulfonate (e.g., a sulfonate group or ion). In various embodiments, the anionic compound may comprise an anionic surfactant. For example, the anionic surfactant may comprise sodium dodecyl benzene sulfonate, sodium xylene sulfonate, benzenesulfonic acid, and/or sodium octane-1-sulphonate monohydrate.

The anionic compound may bind to the cationic functional group of the antimicrobial compound and deactivate the positive charge thereof. The cationic functional group still may remain positively charged, thereby continuing to attract microbes and functioning as an antimicrobial compound. With the positive charge of the cationic functional group deactivated, a method of detecting the presence (or absence) of the antimicrobial compound or coating on a surface (shown in method 300) may comprise measuring the resistance of the surface (step 308) with the antimicrobial system disposed thereon. By measuring the resistance of outer surface 215 (step 308), one may be able to determine the presence (or absence) of first coating 220 and the antimicrobial compound on outer surface 215 (step 312). For example, as the antimicrobial compound or coating is worn or eroded from the surface, and the anionic compound remains, the resistance of the surface may increase.

The resistance of surface 215 (and the antimicrobial system disposed thereon) may be measured in any suitable manner or by any suitable device (e.g., resistance measuring device 250B). For example, the resistance may be measured using a high resistance meter, a resistivity cell, a four-point probe, and/or the like, being applied to (e.g., coupled to and/or in communication with (e.g., electronic communication)) the surface.

In response to receiving a measured resistance value, to determine the presence (or absence) of first coating 220 and the antimicrobial compound on outer surface 215 (step 312), in various embodiments, the measured resistance value may be compared to a reference resistance value (step 310). The reference resistance value may be a value to which a measured resistance value may be compared to aid in determining the presence (or absence) of the antimicrobial compound on the surface. For example, the reference resistance value of the surface may be the resistance value that results from a freshly applied first coating comprising an antimicrobial compound and second coating having the anionic compound (or a first coating and second coating having little or no wear or erosion), referred to herein as a baseline resistance value. The amount of second coating comprising the anionic compound applied to the substrate surface and the antimicrobial coating may be controlled to achieve a desired baseline resistance value (e.g., neutralizing the positive charge of the antimicrobial compound, such that the resistance is zero). Therefore, if the measured resistance value is greater than the baseline resistance value, it may be concluded that at least a portion of the first coating comprising the antimicrobial compound may have been removed. As another example, the reference resistance value may be a threshold resistance value, and in response to the measured resistance value being greater than the threshold resistance value (or differing therefrom beyond a predetermined threshold), reapplication of the antimicrobial coating to the surface may be warranted to replenish the antimicrobial compound thereon to a desired level (e.g., such that the resistance of the surface and the antimicrobial system thereon is below the threshold resistance value). As yet another example, the reference resistance value may be a threshold resistance differential value, which may be predetermined and/or indicate the maximum difference between the measured resistance value and the baseline resistance value before indicating that reapplication of the antimicrobial compound may be appropriate. That is, if the difference between the measured resistance value and the baseline resistance value is beyond the threshold resistance differential value, reapplication of the antimicrobial coating may be warranted.

In response to the measured resistance value indicating that reapplication of the antimicrobial compound may be appropriate (e.g., resistance is greater than a desired level, for example, based on comparing the measured resistance value to the reference resistance value), the antimicrobial compound (or a solution comprising the same) may be reapplied onto the surface (step 314).

The methods and systems discussed herein involving an antimicrobial system (comprising an antimicrobial compound and/or an anionic compound) may allow determination of whether the antimicrobial compound or coating (or a sufficient amount thereof) remains present on a substrate surface by measuring the conductivity and/or resistance of the surface and the coatings thereon. Other antimicrobial detection methods may be less precise or destructive to the underlying substrate (e.g., visual methods, which may result in staining the substrate).

Additionally, in various embodiments, with the conductivity and/or resistance measurements of the surfaces comprising antimicrobial compounds, a quantitative analysis of how much of the remaining antimicrobial compound and/or coating may be determined (e.g., as part of determining the presence or absence of the antimicrobial compound on the substrate surface (step 312)). Such a quantitative analysis may be performed, for example, by comparing the measured value to a pre-established baseline value (such as the baseline conductivity value and baseline resistance value discussed herein). The difference between such values may allow determination of the amount or percentage of antimicrobial compound or coating remaining on the surface, or the amount or percentage of antimicrobial compound or coating that has been lost. Also, such a quantitative analysis may be conducted over a larger surface (e.g., the entire surface area of a surface) than other antimicrobial detection methods, by measuring the surface conductivity or resistance.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method, comprising:
  at least one of:
    measuring, by a conductivity measuring device, a conductivity of a surface of a substrate, or
    measuring, by a resistance measuring device, a resistance of the surface of the substrate;
  comparing, by the conductivity measuring device or the resistance measuring device, the measured conductivity or resistance, respectively, to a reference value; and
  determining, by the conductivity measuring device or the resistance measuring device, a presence or an absence of an antimicrobial system on the surface, wherein the antimicrobial system comprises a first coating, wherein the first coating comprises an antimicrobial compound, wherein the antimicrobial compound comprises a first end and a second end opposite the first end with a hydrocarbon chain therebetween, wherein the antimicrobial compound comprises a cationic functional group on the first end and a silane group on the second end.

2. The method of claim 1, further comprising applying the antimicrobial compound to the surface to form the first coating prior to the measuring the conductivity or the resistance of the surface.

3. The method of claim 1, wherein the measuring the conductivity or the resistance of the surface comprises measuring the conductivity of the first coating resulting from the cationic functional group.

4. The method of claim 3, wherein the reference value comprises a reference conductivity value, wherein, at least one of:
- in response to the measured conductivity value and the reference conductivity value differing beyond a predetermined threshold, the method further comprises reapplying the antimicrobial compound to the surface, or
- in response to the measured conductivity value being less than the reference conductivity value, the method further comprises reapplying the antimicrobial compound to the surface.

5. The method of claim 3, wherein the measuring the conductivity of the first coating is completed via at least one of a voltmeter, a conductivity electrode, or a four-point probe.

6. The method of claim 1, wherein the antimicrobial system comprises an anionic compound.

7. The method of claim 6, wherein the anionic compound comprises a sulfonate.

8. The method of claim 6, wherein the anionic compound is comprised in the first coating.

9. The method of claim 6, wherein the anionic compound is comprised in a second coating comprised in the antimicrobial system, wherein the second coating is disposed on the first coating.

10. The method of claim 6, wherein, in response to the antimicrobial system comprising the anionic compound, the anionic compound binds to the cationic functional group of the antimicrobial compound, deactivating a positive charge of the cationic functional group, and wherein the measuring the conductivity or the resistance of the surface comprises measuring the resistance of the antimicrobial system resulting from the anionic compound.

11. The method of claim 10, wherein the reference value comprises a reference resistance value, wherein, at least one of:
- in response to the measured resistance value and the reference resistance value differing beyond a predetermined threshold, the method further comprises reapplying the antimicrobial compound to the surface, or
- in response to the measured resistance value being greater than the reference resistance value, the method further comprises reapplying the antimicrobial compound to the surface.

12. The method of claim 10, wherein the measuring the resistance of the antimicrobial system is completed via at least one of a high resistance meter, a resistivity cell, or a four-point probe.

13. The method of claim 1, wherein the cationic functional group is a quaternary ammonium group.

14. The method of claim 13, wherein the silane group at least one of binds or couples to the surface of the substrate and the cationic functional group on the first end extends outwardly from the surface of the substrate.

15. The method of claim 1, wherein the surface is an aircraft cabin surface.

16. The method of claim 15, wherein the aircraft cabin surface is comprised in at least one of a passenger seat, a passenger suite, a passenger amenity, a control unit, a stowage/luggage compartment, a lavatory, a self-service bar or kiosk, or a galley.

* * * * *